United States Patent [19]

Farooq et al.

[11] Patent Number: 4,742,056
[45] Date of Patent: May 3, 1988

[54] OXADIAZINONES AND PESTICIDAL USE

[75] Inventors: Saleem Farooq, Arisdorf; Manfred Kühne, Pfeffingen, both of Switzerland

[73] Assignee: Ciba-Geigy Corporation, Ardsley, N.Y.

[21] Appl. No.: 233

[22] Filed: Jan. 2, 1987

[30] Foreign Application Priority Data

Jan. 9, 1986 [CH] Switzerland ............... 37/86
Nov. 28, 1986 [CH] Switzerland ........... 4768/86

[51] Int. Cl.$^4$ ............... A01N 43/72; C07D 273/04
[52] U.S. Cl. ................ 514/229.2; 514/119; 544/67
[58] Field of Search ............. 544/67; 514/119, 228, 514/232

[56] References Cited

U.S. PATENT DOCUMENTS 3,966,721 6/1976 Huff ........................... 260/243 R
4,064,243 12/1977 Huff et al. ..................... 544/67 X

FOREIGN PATENT DOCUMENTS 2459413 7/1975 Fed. Rep. of Germany .
2624341 12/1976 Fed. Rep. of Germany .
630245 6/1982 Switzerland .

OTHER PUBLICATIONS

J. Agr. Food Chem., vol 18, pp. 454–458, John A. Durden (1970).

Primary Examiner—Richard L. Raymond
Attorney, Agent, or Firm—Kevin T. Mansfield; Edward McC. Roberts

[57] ABSTRACT

The invention relates to novel substituted 1,3,5-oxadiazin-2-ones of the formula

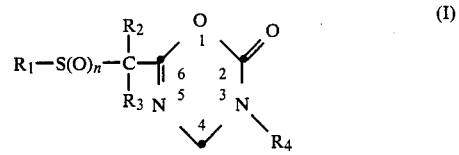

wherein $R_1$ and $R_4$ are each independently of the other $C_1$–$C_8$alkyl, $C_3$–$C_6$-cycloalkyl, $C_3$–$C_4$alkenyl, $C_3$–$C_4$alkynyl, phenyl, or benzyl;

$R_2$ and $R_3$ are each independently of the other hydrogen, $C_1$–$C_4$alkyl, or $R_2$ and $R_3$, together with the carbon atom to which they are attached, are $C_3$–$C_6$-cycloalkyl; and n is 0, 1 or 2;

to the preparation of these compounds and to compositions containing them for use in pest control, in particular for controlling insects and representatives of the order Acarina that attack plants and animals. In particular, the novel compounds are very effective against plant-destructive sucking and feeding insects.

13 Claims, No Drawings

OXADIAZINONES AND PESTICIDAL USE

The present invention relates to novel substituted 6-sulfenylmethyl-1,3,5-oxadiazin-2-ones, 6-sulfinylmethyl-1,3,5oxadiazin-2-ones 6-sulfonylmethyl-1,3,5-oxadiazin-2-ones, to their preparation and to the use thereof in pest control.

The compounds of the present invention have the formula

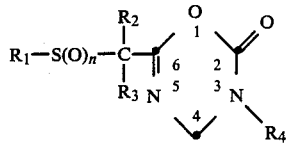

wherein
$R_1$ and $R_4$ are each independently of the other $C_1$–$C_8$alkyl, $C_3$–$C_6$-cycloalkyl, $C_3$–$C_4$alkenyl, $C_3$–$C_4$alkynyl, phenyl or benzyl;
$R_2$ and $R_3$ are each independently of the other hydrogen, $C_1$–$C_4$alkyl, or $R_2$ and $R_3$, together with the carbon atom to which they are attached, are $C_3$–$C_6$-cycloalkyl; and
n is 0, 1 or 2.

Depending on the number of indicated carbon atoms, within the scope of the present invention alkyl shall be understood as meaning straight chain and branched alkyl radicals, e.g. the following groups: methyl, ethyl, propyl, butyl, pentyl, hexyl etc., and the isomers thereof, e.g. isopropyl, isobutyl, tert-butyl, isopentyl etc.

Compounds of formula I which are preferred on account of their activity as pesticides are those wherein
$R_1$ is $C_1$–$C_4$alkyl or phenyl;
$R_2$ and $R_3$ are methyl;
$R_4$ is $C_1$–$C_4$alkyl; and
n is 0, 1 or 2.

Furthermore, compounds of formula I which are valuable on account of their biological activity are those wherein
$R_1$ is methyl or ethyl;
$R_2$ and $R_3$ are methyl;
$R_4$ is $C_1$–$C_3$alkyl; and
n is 0 or 1.

The compounds of formula I can be prepared by cyclising a suitably substituted N-aminomethylacetamide of formula II

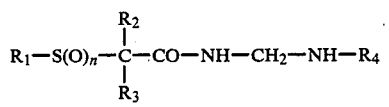

by reaction with phosgene, in which formula II the radicals $R_1$ to $R_4$ and n are as defined above. This process may also be modified by preparing a compound of formula II in situ by reaction of a 2,4,6-hexahydrotriazine of formula III which is suitably substituted in the 1-, 3- and 5-positions.

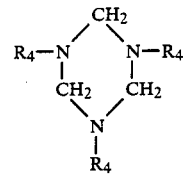

with an acetamide of formula IV

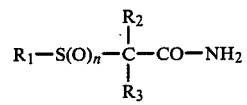

and then reacting the resultant compound of formula II direct with phosgene, in which formulae III and IV the radicals $R_1$ to $R_4$ and n are as defined above.

The above-mentioned cyclisation is carried out by reacting the aminomethylacetamide of formula II with phosgene in the temperature range from $-50°$ C. to $+30°$ C., preferably in the presence of a base and in solvents and/or diluents which are inert towards the reactants, and subsequently effecting the ring closure, preferably in the presence of a base, in the temperature range from $-15°$ C. to $+120°$ C., and, if desired, under pressure.

Suitable solvents or diluents are aliphatic or aromatic hydrocarbons such as benzene, toluene, xylenes, hexane; halogenated hydrocarbons such as chloroform, methylene chloride; ketones such as acetone, methyl ethyl ketone; nitriles such as acetonitrile; dimethylformamide or dimethylsulfone; in particular, however, ethers and ethereal compounds such as dialkyl ethers, dioxane, tetrahydrofuran, 1,2-dimethoxyethane and two-phase mixtures, e.g. water/benzene. Suitable bases are in particular tertiary amines, e.g. trialkylamines, pyridine or pyridine bases, and also NaH or, in the case of aqueous mixtures, alkali metal hydroxides or carbonates or alkaline earth metal hydroxides or carbonates.

As indicated above, the compounds of formula I can also be advantageously prepared (in situ) direct from acetamides of formula IV by a process carried out in a single reaction vessel, which process variant comprises reacting an acetamide of formula IV, in the presence of an anhydrous acid, preferably a hydrohalic acid, e.g. HCl, with a substituted triazine of formula III in an inert organic solvent, and subsequently—without isolating the intermediate of formula II—effecting the cyclisation with phosgene, preferably in the presence of a base. This special embodiment of the process for the preparation of compounds of formula I offers the advantage that those compounds of formula II which are sensitive to acids can also by cyclised without difficulty.

The starting materials of the above formulae II, III and IV are known or can be prepared in conventional manner by methods analogous to known ones (q.v. German Offenlegungsschrift specifications Nos. 2 459 413 and 2 624 341; J. Agr. Food Chem. 18(3), pp. 454–458, 1970).

If the compounds of formula I are obtained by the above-described preparatory processes in the form of 6-sulfenylmethyl or 6-sulfinylmethyl derivatives, i.e. compounds of formula I wherein n is 0 or 1, then these resultant compounds can be oxidised in a manner known per se to give the corresponding 6-sulfonylmethyl derivatives, i.e. compounds of formula I wherein n is 2. Preferred oxidising agents for this purpose are peroxy compounds such as $H_2O_2$ and peracids, e.g. p-chloroperbenzoic acid or peracetic acid. In similar manner, compounds of formula I wherein n is 0 can be oxidised to give compounds of formula I wherein n is 1.

The use of 6-phenyl-1,3,5-oxadiazin-2-ones which may be substituted in the 3-position by alkyl, alkoxyalkyl, alkenyl or cycloalkyl as herbicides and coccidiostats is known from German Offenlegungsschrift No. 2 459 413. Similar compounds are proposed in Swiss patent specification No. 630 245 as supplementary feedstuffs. Furthermore, German Offenlegungsschrift No. 2 624 341 describes 1,3,5-oxadiazin-2-ones substituted in the 6-position by a heterocyclic radical and the use thereof for controlling coccidia.

In contradistinction thereto, the compounds of formula I of the present invention are novel 1,3,5-oxadiazin-2-ones which are substituted in the 3- and 6-positions and whose characteristic structural feature is the presence of a substituted sulfenylmethyl, sulfinylmethyl or sulfonylmethyl group as substituent in the 6-position. Surprisingly, it has been found that the compounds of formula I have excellent properties as pesticides, in particular as insecticides, while being well tolerated by plants and having low toxicity to warm-blooded animals. They are particularly suitable for controlling pests that attack plants and animals.

In particular, the compounds of formula I are suitable for controlling insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina.

The good pesticidal activity of the compounds of formula I of the invention corresponds to a mortality of at least 50–60% of the above pests.

In addition to their favourable action against flies, e.g. *Musca domestica,* and mosquitos, the compounds of formula I are suitable in particular for controlling plant-destructive sucking and feeding insects in ornamentals and crops of useful plants. The compounds of formula I are effective against larval insect stages and nymphs, in particular of harmful feeding insects. Special mention is to be made of the good systemic and contact action of the compounds of formula I, e.g. against pests in crops of fruit, rice and vegetables. If compounds of formula I are ingested by adult insect stages with the feed, then a diminished oviposition and/or reduced hatching rate is observed in many insects, especially in Coleoptera, e.g. *Anthonomus grandis.* In this connection, particular attention is drawn to the fact that the compounds of formula I have both a very pronounced systemic and contact action against sucking insects, in particular against insects of the Aphididae family (e.g. *Aphis fabae, Aphis craccivora* and *Myzus persicae*), which can only be controlled with difficulty using known pesticides. The compounds of formula I can also be used with success against plant-destructive cidadas, especially in rice crops, e.g. against *Nilaparvata lugens, Laodelphax striatellus* and Nephotettix.

The compounds of formula I can also be used for controlling ectoparasites, e.g. *Lucilia sericata,* and ticks in domestic animals and productive livestock, e.g. by treating animals, cowsheds, barns, stables, etc., and pastures.

In addition, it has been found that combinations of compounds of formula I with other insecticides and/or acaricides (e.g. organophosphorus compounds); imido ethers; amidines; amines; hydrazines; triazines; ureas; pyrethrinoids and diphenylmethane derivatives and carbamates) in a weight ratio in the range from 5:1 to 1:5, preferably 1:1, have a potentiating or synergising effect against various pests of animals and plants, in particular against plant-destructive insects, which effect, surprisingly, greatly exceeds the additive effect of these combined active ingredients. This potentiating effect or synergism of the combined active ingredients occurs in all control procedures. Methods of control of the present invention may comprise applying the active ingredients either in premixed form from one container or at short intervals in succession or simultaneously from different containers to the habitat of the pests or to the pests themselves.

Compounds of formula I produce a potentiating or synergising effect in particular in admixture with e.g. the following known insecticides or acaricides:

1. Organic phosphates:
   1.1 Alkyl(acyl)phosphates:
   acephate; methamidophos; ethoprophos; disulfoton; TEPP; naled; carbophenothion; trichlorphon; ethion; sulfotep; mipafox; vamidothion; phenkapton; terbufos; chlormephos; phoxim; phorate and fospargyl.

1.2 Carbonyl alkyl phosphates:
   phenthoate; dimethoate; malathion; morphothion and formothion.

1.3 Vinyl phosphates:
   tetrachlorvinphos; propetamphos; methacrifos; chlorfenvinphos; tetrachlorvinphos ethyl; Thiophosdrin ®; mevinphos; crotoxyphos; phosphamidon; dicrotophos; monocrotophos; dichlorvos; Fosfinon ®; Akton ®; Bomyl ®, bromfenvinphos and heptenophos.

1.4 Aromatic phosphates:
   profenofos; trifenophos; bromophos; mercaptoprophos; methylparathion; parathion; chlorthion; fenitrothion; fenchlorphos; fenthion; cyanophos; dichlofenthion; fenamiphos; fonofos; jodfenfos; temephos; prothiophos; isofenphos; fensulfothion and lepthophos.

1.5 Heterocyclic phosphates:
   isazophos; triazophos; chlorpyrifos; phosmet; azamethiphos; phosalon; azinphos methyl; azinphos ethyl; dialifos; dioxathion; diazinon; methidathion; isoxathion; chlorpyrofos methyl; phosfolan; fosthietan; etrimfos; pyridafenthion; mephosfolan; thionazin; zolaprofos and pyrimiphos methyl.

2. Carbamates:
   2.1 Aromatic carbamates:
   dioxacarb; methiocarb; isoprocarb; carbaryl; xylylcarb; CPMC, bufencarb; BPMC; carbofuran; propoxur, ethiofencarb; carbosulfan; Mydrol ®; bendiocarb; aminocarb; chloetocarb and benzofuracarb.

2.2 Heterocyclic carbamates:
   Isolan ®; dimetilan; primicarb; hyquincarb; methomyl; aldicarb; Tirpat ®; demethyl oxamyl; thiodicarb; nitrilacarb; oxamyl; thiofanox and butocarboxim.

3. Diphenylmethane derivates:
   DDT; methoxychlor; prolan; bulan; chlorobenzilate; chloropropylate and bromopropylate.

4. Amidines, imido ethers, amines, hydrazines:
   chlordimeform; benzomate and amitraz.

5. Pyrethrinoids:
   resmethrin; permethrin; phenothrin; cypermethrin; decamethrin; fenpropathrin; fenfluthrin; fenpyrithrin;

cyhalothrin; flumethrin; cyfluthrin; fenvalerate; fluvalinate and flucytrin.

6. Ureas and triazines:
diflubenzuron; flucarbenzuron and cyromazin.

The compounds of formula I or the combinations or synergistic mixtures thereof with other active ingredients are used in unmodified form, or preferably together with the adjuvants conventionally employed in the art of formulation, and are therefore formulated in known manner e.g. to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g., xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$-$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenyl with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or a combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower active ingredient concentrations.

The compositions may also contain further ingredients, such as stabilisers, antifoams, viscosity regulators, binders, tackifiers as well as fertilisers or other active ingredients for obtaining special effects.

EXAMPLE 1

Preparation of 6-(1-methyl-1-methylsulfenylethyl)-3-isopropyl-3,4-dihydro-2H-1,3,5-oxadiazin-2-one 5 g of gaseous hydrogen chloride are introduced at −30° C. into 300 ml of dimethoxyethane, followed by the addition of 6.4 g of 1,3,5-triisopropyl-2,4,6-hexahydrotriazine. The reaction mixture is kept at −20° C., during which time 12 g of α-methylmercaptoisobutyric acid amide are added. The reaction mixture is stirred for 2½ hours at room temperature. Then, likewise at −20° C., 50 ml of a 20% phosgene solution in toluene and, subsequently, a solution of 15 ml of pyridine in 30 ml of dimethoxyethane are added dropwise to the reaction mixture. The mixture is then stirred for 1 hour at room temperature. A further 30 ml of pyridine are then added dropwise, and the mixture is stirred for a further 4 hours at 60° C. For working up, the reaction mixture is cooled and filtered, and the filtrate is concentrated by evaporation. The residue is taken up in ethyl acetate, and the resultant solution is extracted twice with water and twice with a saturated sodium chloride solution. The separated organic phase is dried over sodium sulfate and concentrated by evaporation. The residue is taken up in hexane, a small amount of silica gel is added, and the batch is filtered. The filtrate is concentrated by evaporation, thus affording the title compound of the formula

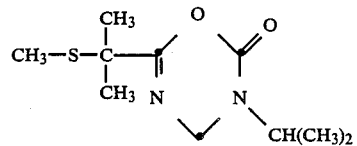

with a refractive index $n_D^{20}$ of 1.5028 (compound 1).

EXAMPLE 2

Preparation of 6-(1-methyl-1-methylsulfinylethyl)-3-isopropyl-3,4-dihydro-2H-1,3,5-oxadiazin-2-one 11.5 g of 6-(1-methyl-1-methylmercaptoethyl)-3-isopropyl-3,4-dihydro-2H-1,3,5-oxadiazin-2-one (Example 1) are dissolved in 100 ml of chloroform. The resultant solution is cooled to −10° C., and a solution of 9.5 g of m-chloroperbenzoic acid in 120 ml of chloroform is then added dropwise. The reaction mixture is subsequently stirred for 1 hour at room temperature and then concentrated. The residual crude product is recrystallised from a 1:1 mixture of ethyl acetate and hexane, affording the title compound of the formula

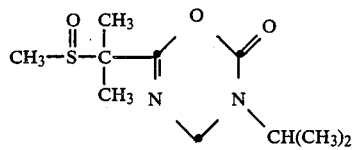

with a melting point of 120-°121° C. (compound 2).

EXAMPLE 3

Preparation of 6-(1-methyl-1-methylsulfonylethyl)-3-methyl-3,4-dihydro-2H-1,3,5-oxadiazin-2-one 20.2 g of 6-(1-methyl-1-methymercaptoethyl)-3-methyl-3,4,-dihydro-2H-1,3,5-oxadiazin-2-one are dissolved in 100 ml of chloroform, and the resultant solution is cooled to 0° C. Over about 15 minutes, 16 ml of a 40% peracetic acid solution are added dropwise to the cooled solution, during which time the reaction temperature is allowed to increase to about 40° C. A further 16 ml of 40% peracetic acid solution are subsequently added. The reaction mixture is stirred for 10 hours at room temperature and then poured into an ice/water mixture. The separated chloroform phase is washed twice with water, dried over Na₂SO₄ and filtered, and the filtrate is concentrated. The residual crude product is washed with a small amount of water and dried over KOH at 40° C., affording the desired title compound of the formula

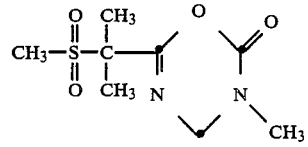

with a melting point of 134°-136° C. (compound 3).

The following compounds of formula I are prepared in accordance with the above-described procedures:

| Compound | R₁ | R₂ | R₃ | R₄ | n | Physical data |
|---|---|---|---|---|---|---|
| 4 | CH₃— | CH₃— | CH₃— | CH₃— | 0 | m.p.: 86-87° C. |
| 5 | CH₃— | CH₃— | CH₃— | CH₃— | 1 | m.p.: 84-89° C. |
| 6 | n-C₈H₁₇— | CH₃— | CH₃— | CH₃— | 0 | m.p.: 33-34° C. |
| 7 | C₂H₅— | CH₃— | CH₃— | CH₃— | 0 | m.p.: 49-50° C. |
| 8 | C₂H₅— | CH₃— | CH₃— | CH₃— | 1 | m.p.: 66-68° C. |
| 9 | n-C₈H₁₇— | CH₃— | CH₃— | CH₃— | 1 | clear oil |
| 10 | i-C₃H₇— | CH₃— | CH₃— | CH₃— | 0 | m.p.: 84-87° C. |
| 11 | i-C₃H₇— | CH₃— | CH₃— | CH₃— | 1 | m.p.: 76-78° C. |
| 12 | n-C₄H₉— | CH₃— | CH₃— | CH₃— | 0 | light-coloured oil |

-continued

| Compound | $R_1$ | $R_2$ | $R_3$ | $R_4$ | n | Physical data |
|---|---|---|---|---|---|---|
| 13 | cyclohexyl-H | $CH_3-$ | $CH_3-$ | $CH_3-$ | 0 | m.p.: 68–70° C. |
| 14 | $CH_2=CH-CH_2-$ | $CH_3-$ | $CH_3-$ | $CH_3-$ | 0 | m.p.: 38–40° C. |
| 15 | $CH_3-$ | $CH_3-$ | $CH_3-$ | $n-C_3H_7-$ | 0 | $n_D^{20} = 1.5051$ |
| 16 | $CH_3-$ | $CH_3-$ | $CH_3-$ | $C_2H_5-$ | 0 | m.p.: 38–40° C. |
| 17 | $CH_3-$ | $CH_3-$ | $CH_3-$ | $n-C_4H_9-$ | 0 | $n_D^{20} = 1.5522$ |
| 18 | $CH_3-$ | $CH_3-$ | $CH_3-$ | $s-C_4H_9-$ | 0 | $n_D^{20} = 1.4929$ |
| 19 | $CH_3-$ | $CH_3-$ | $CH_3-$ | $i-C_4H_9-$ | 0 | $n_D^{20} = 1.4989$ |
| 20 | $CH_3-$ | $CH_3-$ | $CH_3-$ | $t-C_4H_9-$ | 0 | $n_D^{20} = 1.4994$ |
| 21 | $CH_3-$ | $CH_3-$ | $CH_3-$ | $n-C_8H_{17}-$ | 0 | $n_D^{20} = 1.4872$ |
| 22 | $CH_3-$ | $CH_3-$ | $CH_3-$ | cyclopropyl-CH | 0 | m.p.: 72–73° C. |
| 23 | $C_2H_5-$ | $CH_3-$ | $CH_3-$ | $i-C_3H_7-$ | 0 | $n_D^{20} = 1.4982$ |
| 24 | $i-C_3H_7-$ | $CH_3-$ | $CH_3-$ | $i-C_3H_7-$ | 0 | $n_D^{20} = 1.4942$ |
| 25 | $CH_3-$ | $CH_3-$ | $CH_3-$ | $i-C_3H_7-$ | 2 | |
| 26 | $CH_3-$ | $CH_3-$ | $CH_3-$ | $i-C_4H_9-$ | 1 | |
| 27 | $CH_3-$ | $CH_2-CH_2-$ | | $CH_3-$ | 0 | m.p.: 61–63° C. |
| 28 | $CH_3-$ | $CH_2-CH_2-$ | | $CH_3-$ | 1 | |
| 29 | $CH_3-$ | $CH_2-CH_2-$ | | $CH_3-$ | 2 | |
| 30 | $CH_3-$ | $CH_2-CH_2-$ | | $i-C_3H_7-$ | 0 | $n_D^{20} = 1.5151$ |
| 31 | $CH_3-$ | $CH_2-CH_2-$ | | $i-C_3H_7-$ | 1 | m.p.: 117–119° C. |
| 32 | $CH_3-$ | $CH_2-CH_2-$ | | $i-C_3H_7-$ | 2 | |
| 33 | $CH_3-$ | $-CH_2-(CH_2)_3-CH_2-$ | | $C_2H_5-$ | 0 | |
| 34 | $CH_3-$ | $-CH_2-(CH_2)_3-CH_2-$ | | $C_2H_5-$ | 1 | |
| 35 | $CH_3-$ | $-CH_2-(CH_2)_3-CH_2-$ | | $C_2H_5-$ | 2 | |
| 36 | $CH_3-$ | $-CH_2-(CH_2)_3-CH_2-$ | | $i-C_3H_7-$ | 0 | |
| 37 | $CH_3-$ | $-CH_2-(CH_2)_3-CH_2-$ | | $i-C_3H_7-$ | 1 | |
| 38 | $CH_3-$ | $-CH_2-(CH_2)_3-CH_2-$ | | $i-C_3H_7-$ | 2 | |
| 39 | $CH_3-$ | $-CH_2-CH_2-CH_2-$ | | $i-C_3H_7-$ | 0 | $n_D^{20} = 1.5189$ |
| 40 | $CH_3-$ | $-CH_2-CH_2-CH_2-$ | | $CH_3-$ | 0 | m.p.: 96–98° C. |
| 41 | $CH_3-$ | $-CH_2-CH_2-CH_2-$ | | $i-C_3H_7-$ | 1 | m.p.: 97–99° C. |
| 42 | $CH_3-$ | $-CH_2-CH_2-CH_2-$ | | $CH_3-$ | 0 | |
| 43 | $CH_3-$ | $-CH_2-(CH_2)_3-CH_2-$ | | $CH_3-$ | 0 | |
| 44 | $CH_3$ | $-CH_2-(CH_2)_3-CH_2-$ | | $CH_3-$ | 1 | |
| 45 | $CH_3-$ | $-CH_2-CH_2-CH_2-$ | | $CH_3-$ | 1 | m.p.: 105–107° C. |
| 46 | $n-C_4H_9-$ | $CH_3-$ | $CH_3-$ | $i-C_3H_7-$ | 0 | $n_D^{20} = 1.4919$ |
| 47 | $s-C_4H_9-$ | $CH_3-$ | $CH_3-$ | $i-C_3H_7-$ | 0 | $n_D^{20} = 1.4943$ |
| 48 | $i-C_4H_9-$ | $CH_3-$ | $CH_3-$ | $i-C_3H_7-$ | 0 | |
| 49 | $t-C_4H_9-$ | $CH_3-$ | $CH_3-$ | $i-C_3H_7-$ | 0 | m.p.: 79–81° C. |
| 50 | $n-C_5H_{11}-$ | $CH_3-$ | $CH_3-$ | $i-C_3H_7-$ | 0 | $n_D^{20} = 1.4931$ |
| 51 | $n-C_3H_7-$ | $CH_3-$ | $CH_3-$ | $i-C_3H_7-$ | 0 | $n_D^{20} = 1.4941$ |
| 52 | $n-C_4H_9-$ | $CH_3-$ | $CH_3-$ | $i-C_3H_7-$ | 0 | $n_D^{20} = 1.5065$ |
| 53 | $s-C_4H_9-$ | $CH_3-$ | $CH_3-$ | $i-C_3H_7-$ | 1 | $n_D^{20} = 1.5071$ |
| 54 | $t-C_4H_9-$ | $CH_3-$ | $CH_3-$ | $i-C_3H_7-$ | 1 | m.p.: 80–82° C. |
| 55 | $n-C_5H_{11}-$ | $CH_3-$ | $CH_3-$ | $i-C_3H_7-$ | 1 | $n_D^{20} = 1.5039$ |
| 56 | $n-C_3H_7-$ | $CH_3$ | $CH_3-$ | $i-C_3H_7-$ | 1 | $n_D^{20} = 1.5068$ |
| 57 | $s-C_4H_9-$ | $CH_3$ | $CH_3-$ | $CH_3-$ | 0 | $n_D^{20} = 1.5011$ |
| 58 | $i-C_4H_9-$ | $CH_3-$ | $CH_3-$ | $CH_3-$ | 0 | $n_D^{20} = 1.5002$ |
| 59 | $t-C_4H_9-$ | $CH_3-$ | $CH_3-$ | $CH_3-$ | 0 | m.p.: 78–82° C. |
| 60 | $n-C_5H_{11}-$ | $CH_3-$ | $CH_3-$ | $CH_3-$ | 0 | $n_D^{20} = 1.4994$ |
| 61 | $n-C_3H_7-$ | $CH_3-$ | $CH_3-$ | $CH_3-$ | | $n_D^{20} = 1.5049$ |
| 62 | $s-C_4H_9-$ | $CH_3-$ | $CH_3-$ | $CH_3-$ | 1 | $n_D^{20} = 1.5152$ |
| 63 | $i-C_4H_9-$ | $CH_3-$ | $CH_3-$ | $CH_3-$ | 1 | $n_D^{20} = 1.5102$ |
| 64 | $t-C_4H_9-$ | $CH_3-$ | $CH_3-$ | $CH_3-$ | 1 | m.p.: 101–103° C. |
| 65 | $n-C_5H_{11}-$ | $CH_3-$ | $CH_3-$ | $CH_3-$ | 1 | $n_D^{20} = 1.5059$ |
| 66 | $n-C_3H_7-$ | $CH_3-$ | $CH_3-$ | $CH_3-$ | 1 | m.p.: 60–62° C. |
| 67 | $C_2H_5-$ | $CH_3-$ | $CH_3-$ | $i-C_3H_7-$ | 1 | $n_D^{20} = 1.5100$ |
| 68 | $i-C_3H_7-$ | $CH_3-$ | $CH_3-$ | $i-C_3H_7-$ | 1 | $n_D^{20} = 1.5068$ |

EXAMPLE 4

Formulations for liquid active ingredients of formula I according to Examples 1 to 3 or combinations thereof with other insecticides or acaricides (throughout, percentages are by weight)

| 1. Emulsifiable concentrates | (a) | (b) | (c) |
|---|---|---|---|
| active ingredient or active ingredient combination | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexane | — | 15% | 20% |

-continued

| 1. Emulsifiable concentrates | (a) | (b) | (c) |
|---|---|---|---|
| xylene mixture | 65% | 25% | 20% |

Emulsion of any required concentration can be produced from such concentrates by dilution with water.

| 2. Solutions | (a) | (b) | (c) | (d) |
|---|---|---|---|---|
| active ingredient or active ingredient combination | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| expoxidised coconut oil | — | — | 1% | 5% |
| ligroin (boiling range 160–190°) | — | — | 94% | — |

These solutions are suitable for application in the form of microdrops.

| 3. Granulates | (a) | (b) |
|---|---|---|
| active ingredient or active ingredient combination | 5% | 10% |
| kaolin | 94% | — |
| highly dispersed silicic acid | 1% | — |
| attapulgite | — | 90% |

The active ingredient or active ingredient combination is dissolved in methylene chloride, the solution is sprayed onto the carrier, and the solvent is subsequently evaporated off in vacuo.

| 4. Dusts | (a) | (b) |
|---|---|---|
| active ingredient or active ingredient combination | 2% | 5% |
| highly dispersed silicic acid | 1% | 5% |
| talcum | 97% | — |
| kaolin | — | 90% |

Ready for use dusts are obtained by intimately mixing the carriers with the active ingredient or active ingredient combination.

Formulations for solid active ingredients of formula I according to Examples 1 to 3 or combinations thereof with other insecticides or acaricides (throughout, percentages are by weight)

| 1. Wettable powders | (a) | (b) | (c) |
|---|---|---|---|
| active ingredient or active ingredient combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or active ingredient combination is thoroughly mixed with the adjuvants and the mixture is thoroughly ground in a suitable mill, affording wettable powders which can be diluted with water to give suspensions of any desired concentration.

| 2. Emulsifiable concentrate | |
|---|---|
| active ingredient or active ingredient combination | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | (a) | (b) |
|---|---|---|
| active ingredient or active ingredient combination | 5% | 8% |
| talcum | 95% | — |
| kaolin | — | 92% |

Ready for use dusts are obtained by mixing the active ingredient or active ingredient combination with the carrier, and grinding the mixture in a suitable mill.

| 4. Extruder granulate | |
|---|---|
| active ingredient or active ingredient combination | 10% |
| sodium lignosulfonate | 2% |
| carboxymethylcellulose | 1% |
| kaolin | 87% |

The active ingredient or active ingredient combination is mixed and ground with the adjuvants, and the mixture is subsequently moistened with water. The mixture is extruded, granulated and then dried in a stream of air.

| 5. Coated granulate | |
|---|---|
| active ingredient or active ingredient combination | 3% |
| polyethylene glycol (mol. wt. 200) | 3% |
| kaolin | 94% |

The finely ground active ingredient or active ingredient combination is uniformly applied, in a mixer, to the kaolin moistened with polyethylene glycol. Non-dusty coated granulates are obtained in this manner.

| 6. Suspension concentrate | |
|---|---|
| active ingredient or active ingredient combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or active ingredient combination is intimately mixed with the adjuvants, giving a suspension concentrate from which suspensions of any desired concentration can be obtained by dilution with water.

EXAMPLE 5

Action against *Musca domestica*

50 g of freshly prepared CMSA nutrient substrate for maggots are charged into each of a number of beakers. A specific amount of an acetonic solution containing 1% by weight of the respective test compound is pipetted onto the nutrient substrate present in the beakers to give an active ingredient concentration of 800 ppm. The substrate is then throughly mixed and the acetone subsequently allowed to evaporate over a period of at least 20 hours.

Then 25 one-day-old maggots of *Musca domestica* are put into each of the beakers containing the treated nutrient substrate for testing with each active ingredient at the given concentration. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

Compounds of formula I according to Examples 1 to 3 exhibit good activity in this test.

EXAMPLE 6

Action against *Lucilia sericata*

1 ml of an aqueous formulation containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

In this test, compounds of formula I according to Examples 1 to 3 exhibit good activity against *Lucilia sericata*.

EXAMPLE 7

Action against *Aedes aegypti*

A concentration of 800 ppm is obtained by pipetting a specific amount of a 0.1% solution of the test compound in acetone onto the surface of 150 ml of water in a beaker. After the acetone has evaporated, 30 to 40 two-day old larvae of *Aedes aegypti* are put into the beaker containing the test compound. Mortality counts are made after 2 and 7 days.

Compounds of formula I according to Examples 1 to 3 exhibit good activity in this test.

EXAMPLE 8

Influence on the reproduction of *Anthonomus grandis*

*Anthonomus grandis* adults which are not more than 24 hours old after hatching are transferred in groups of 25 to barred cages. The cages are then immersed for 5 to 10 seconds in an acetonic solution containing 800 ppm by weight of the test compound. After the beetles have dried, they are placed in covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. A count is made after 7 days to determine the percentage mortality of the eggs, i.e. how many larvae have developed from the eggs.

The duration of the reproduction inhibiting effect of the test compounds is determined by monitoring the egg deposits of the beetles further, i.e. over a period of about 4 weeks. Evaluation is made by assessing the reduction in the number of deposited eggs and larvae hatched from them in comparison with untreated controls.

Compounds of formula I according to Examples 1 to 3 exhibit good activity in this test.

EXAMPLE 9

Contact action against *Aphis craccivora*

Before the start of the test, 4- to 5-day old bean seedlings (*Vicia faba*) reared in pots are each populated with about 200 insects of the species *Aphis craccivora*. The treated plants are sprayed direct to drip point 24 hours later with an aqueous formulation containing 12.5 ppm of the test compound. Two plants are used for each test compound at its given concentration. A mortality count is made after 24 and 72 hours respectively. The test is carried out at 21°-22° C. and at a relative humidity of about 55%.

In the test, compounds 1 and 2 according to Examples 1 and 2 effect 90 to 100% mortality.

EXAMPLE 10

Systemic action against *Aphis craccivora* (in water)

Pea seedlings about 1 to 2 cm in height which had been infested with a population of the aphids 24 hours before the beginning of the test are placed in 20 ml of an aqueous mixture containing the test compound. The aqueous mixture is prepared from an emulsifiable concentrate or a wettable powder formulation of the test compound and is contained in a vessel which is closed with a perforated plastic lid. The roots of each of the infested pea plantlets are pushed through a hole in the plastic lid into the mixture containing the test substance. Each hole is then sealed with cotton wool to fix the plant and to prevent the aphids from being affected by the test substance via the gas phase.

The test is carried out at 20° C. and at 60% relative humidity. After two days an evaluation is made of the number of test organisms which are no longer capable of sucking as compared with untreated controls, thereby establishing whether the test substance absorbed via the roots kills the aphids at the upper parts of the plants.

In this test, 90 to 100% mortality is effected against *Aphis craccivora* by compound 1 according to Example 1 at 12.5 ppm and by compound 2 according to Example 2 at 0.75 ppm.

EXAMPLE 11

Contact action against *Myzus persicae*

4- to 5-day old bean seedlings (*Vicia faba*) which have been reared in water are each populated with about 200 aphids of the species *Myzus persicae* before the start of the test. The treated plants are sprayed direct to drip point 24 hours later with an aqueous suspension containing the test compound in a concentration of 50 or 100 ppm. Two plants are used for each compound at its given concentration. An evaluation of percentage mortality is made 24 and 72 hours respectively after application. The test is carried out at 21°-22° C. and about 60% relative humidity.

In this test, compounds 1 and 2 according to Examples 1 and 2 respectively effect 90 to 100% mortality.

EXAMPLE 12

Systemic action against *Myzus persicae* (in soil)

Cabbage plants which have grown roots are transplanted in the 4- to 5-leaf stage into pots containing 60 ccm of soil. Then 50 ml of an aqueous formulation (prepared from a 25% wettable powder of the respective test compound in a concentration of 800 ppm are poured direct onto the soil without wetting the plant itself.

After 24 hours the parts of the treated plants above the soil are populated with aphids of the species *Myzus persicae* and plastic cylinders are then slipped over the plants to protect the aphids from any possible contact with the test substance either directly or via the gas phase.

The evaluation of percentage mortality is made 48 hours after the start of the test. Two plants, each in a separate pot, are used for each test substance at its given concentration. The test is carried out at about 25° C. and 60% relative humidity.

Compounds of formula I according to Examples 1 to 3 exhibit good activity in this test.

EXAMPLE 13

Leaf penetration action against *Aphis craccivora*

A small shoot of *Vicia faba*, which is highly infested with aphids of the species *Aphis craccivora*, is placed in each of a number of 8 cm high plastic beakers (diameter about 6 cm). Each beaker is covered with a plastic lid having a punched opening of 2 cm diameter in the centre. A leaf of a *Vicia faba*-plant is then placed over the opening in the lid without separating this leaf from the potted plant. The leaf is then fixed on the beaker with a second punched lid above the opening of the first lid. From underneath, i.e. through the opening of the first lid, the aphids in the beaker then infect the leaf of the plant used as bait. An aqueous formulation of the test compound is then applied in a concentration of 800 ppm uniformly with a brush to the top side of the leaf. An investigation is then made to determine whether the test substance applied to the top side of the leaf of the plant used as bait has diffused in sufficient amount through the leaf to its underside to kill aphids sucking thereon.

The test is carried out at about 20° C. and 60% relative humidity. The evaluation of percentage mortality is made 48 hours after application of the test compound.

Compounds of formula I according to Examples 1 to 3 exhibit good activity in this test.

EXAMPLE 14

Action against *Diabrotica balteata* (in soil)

350 ml of soil (consisting of 95 vol.% of sand and 5 vol.% of peat) are mixed with 150 ml of an aqueous emulsion formulation which contains the test compound in a concentration of 12.5 ppm. Plastic beakers with a diameter of about 10 cm at the top are then partly filled with the treated soil. Ten $L_3$-larvae of *Diabrotica balteata* are put into each beaker, then 4 maize seedlings are planted and the beaker is filled up with soil. The beakers are sealed with plastic sheeting and kept at about 22° C. Ten days later the soil in the beakers is sieved and a mortality count of the remaining larvae is made.

Compound 1 according to Example 1 effects 80 to 100% mortality in this test.

EXAMPLE 15

Action against *Diabrotica balteata* (in water)

5 maize seedlings 1 to 3 cm in height and a filter paper disc are immersed in an aqueous solution containing the test compound in a concentration of 12.5 ppm and about 4 vol.% of acetone. The immersed filter paper disc is placed at the bottom of a plastic beaker (capacity 200 ml). A dry filter paper disc together with the maize seedlings and 10 *Diabrotica balteata* larvae in the $L_2$- or $L_3$-stage are then placed on the first disc. The test is carried out at about 24° C. and at 40–60% relative humidity and in daylight. Evaluation is made 6 days later in comparison with untreated controls.

Compound 1 according to Example 1 effects 80 to 100% mortality in this test.

EXAMPLE 16

Action against *Laodelphax striatellus* and *Nilaparvata lugens* (nyymphs)

The test is carried out with growing plants. For this purpose 4 rice plants (thickness of stem 8 mm) about 20 cm in height are planted into each of a number of pots (diameter 8 cm). The plants in each pot are sprayed on a rotary table with 100 ml of an acetonic solution containing 400 ppm of the respective test compound. After the spray coating has dried, each plant is populated with 20 nymphs of the test organisms in the third stage. To prevent the cicadas from escaping, a glass cylinder open at both ends is slipped over each of the plants and sealed with a gauze top. The nymphs are kept for 10 days on the treated plant until the next development stage has been reached. Evaluation of percentage mortality is made 1, 4 and 8 days after treatment.

In this test, 80 to 100% mortality is effected against Nilaparvata by compound 1 according to Example 1 at 400 ppm and by compound 2 according to Example 2 at 200 ppm.

In this test, the compounds of formula I also exhibit good activity against *Laodelphax striatellus*.

EXAMPLE 17

Systemic action against *Nilaparvata lugens* (nymphs)

The test is carried out with growing 10- to 14-day-old rice plants in pots (diameter 5.5 cm) filled with soil.

5 ml of an aqueous emulsion formulation containing the respective test compound in a concentration of 12.5 ppm is poured onto the soil in each of the pots. One week later each of the treated plants is populated with 20 nymphs of *Nilaparvata lugens* in the $N_3$-stage. Six days afterwards, the percentage mortality of the test insects is determined in comparison with untreated controls.

The test is carried out at about 23° C. and at 60% relative humidity. The plants are exposed to light for a period of 14 hours per day.

In this test, compounds 1 and 2 according to Examples 1 and 2 respectively effect 80 to 100% mortality at 12.5 ppm.

EXAMPLE 18

Potentiation of the insecticidal action against *Myzus persicae*

The following test compounds were used:

Compound A:
compound 1 of the present invention according to Example 1 of the formula

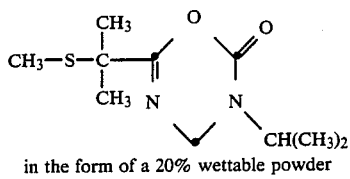

in the form of a 20% wettable powder

Compound B:
Phosphamidon of the formula

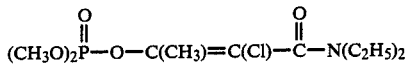

(described in U.S. Pat. No. 2,908,605) in the form of a 20% wettable powder.

Test procedure

Before the beginning of the test, red pepper and pea seedlings about 4 cm in height which have been reared in water are each populated with about 200 individuals of the species Myzus persicae. 24 hours later the treated plants are sprayed to drip point with aqueous suspensions containing increasing amounts of the test compounds A and B or of a combination thereof. Two plants are used for each test substance at its given concentration. An evaluation of the percentage mortality is made 48 hours after application. The test is carried out at 20°-22° C. and at 60% relative humidity.

Test results:

| Compounds employed | % Mortality (on red peppers) Active ingredient concentration | | |
|---|---|---|---|
| | 100 ppm | 50 ppm | 25 ppm |
| compound A | 0% | 0% | 0% |
| compound B | 58% | 0% | 0% |
| combination A + B* | 100% | 94% | 82% |

*(1:1; i.e. 50/25/12.5 ppm of each of components A and B in the spray solution)

| Compounds employed | % Mortality (on peas) Active ingredient concentration | | |
|---|---|---|---|
| | 400 ppm | 200 ppm | 100 ppm |
| compound A | 65% | 0% | 0% |
| compound B | 88% | 0% | 0% |
| combination A + B* | 100% | 100% | 88% |

*(1:1; i.e. 200/100/50 ppm of each of components A and B in the spray solution)

EXAMPLE 19

Action against Nephotettix cincticeps (nymphs)

The test is carried out with growing plants. For this purpose approximately twenty-day-old rice plants about 15 cm in height are planted into each of a number of pots (diameter: 5.5 cm).

The plants in each pot are sprayed on a rotary table with 100 ml of an acetonic solution containing 12.5, 50, 100, 200 or 400 ppm of compound 2. After the spray coating has dried, each plant is populated with 20 nymphs of the test organisms in the second or third stage. To prevent the cicadas from escaping, a plexiglass cylinder is slipped over each of the plants and sealed with a gauze top. The nymphs are kept for 5 days on the treated plants, which have to be resprayed at least once. The test is carried out at a temperature of about 23° C. and at 55% relative humidity. The plants are exposed to light for a period of 16 hours per day.

On the sixth day, the mortality rate of the test organisms on plants which have been sprayed with 50 ppm or more of active ingredient is established as being at least 80%.

What is claimed is:

1. A compound of formula I

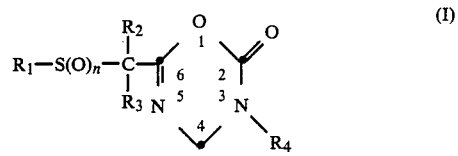

wherein
$R_1$ and $R_4$ are each independently of the other $C_1$-$C_8$alkyl, $C_3$-$C_6$cycloalkyl, $C_3$-$C_4$alkenyl, $C_3$-$C_4$alkynyl, phenyl or benzyl;
$R_2$ and $R_3$ are each independently of the other hydrogen, $C_1$-$C_4$alkyl, or $R_2$ and $R_3$, together with the carbon atom to which they are attached, are $C_3$-$C_6$cycloalkyl; and
n is 0, 1 or 2.

2. A compound of formula I according to claim 1, wherein
$R_1$ is $C_1$-$C_4$alkyl or phenyl;
$R_2$ and $R_3$ are methyl;
$R_4$ is $C_1$-$C_4$alkyl; and
n is 0, 1 or 2.

3. A compound of formula I according to claim 1, wherein
$R_1$ is methyl or ethyl;
$R_2$ and $R_3$ are methyl;
$R_4$ is $C_1$-$C_3$alkyl; and
n is 0 or 1.

4. The compound according to claim 1 of the formula

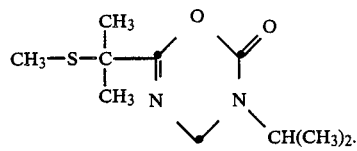

5. The compound according to claim 1 of the formula

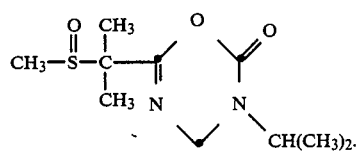

6. The compound according to claim 1 of the formula

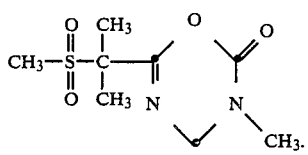

7. The compound according to claim 1 of the formula

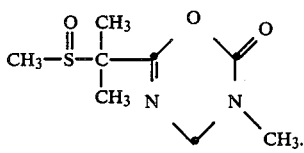

8. The compound according to claim 1 of the formula

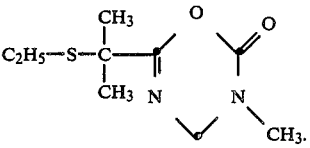

9. The compound according to claim 1 of the formula

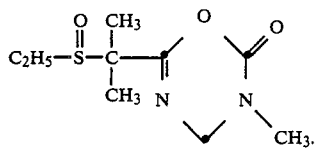

10. A pesticidal composition which contains as active ingredient a compound of formula I according to claim 1, together with suitable carriers and/or other adjuvants.

11. A composition according to claim 10 with potentiating or synergistic action, which composition contains as active ingredient, in addition to a compound of formula I, a further insecticidal and/or acaricidal substance.

12. A composition according to claim 10, which contains as active ingredients a compound of formula I and phosphamidon.

13. A method of controlling insects and representatives of the order Acarina, which method comprises contacting or treating said pests or their eggs and/or their various development stages or the locus thereof with a pesticidally effective amount of a compound of formula I according to claim 1.

* * * * *